United States Patent

Grünewald

[11] Patent Number: 5,986,264
[45] Date of Patent: Nov. 16, 1999

[54] ION BEAM PREPARATION DEVICE FOR ELECTRON MICROSCOPY

[75] Inventor: Wolfgang Grünewald, Chemnitz, Germany

[73] Assignee: Bal-Tec A.G., Balzers, Liechtenstein

[21] Appl. No.: 08/945,391

[22] PCT Filed: Apr. 22, 1996

[86] PCT No.: PCT/CH96/00145

§ 371 Date: Oct. 14, 1997

§ 102(e) Date: Oct. 14, 1997

[87] PCT Pub. No.: WO96/35226

PCT Pub. Date: Nov. 7, 1996

[30] Foreign Application Priority Data

Apr. 29, 1995 [DE] Germany ................ 295 07 225 U

[51] Int. Cl.⁶ ............................. H01J 37/30; H01J 37/26
[52] U.S. Cl. ................................ 250/310; 250/492.21
[58] Field of Search ................... 250/492.21, 492.2, 250/309, 310

[56] References Cited

U.S. PATENT DOCUMENTS

| | | | |
|---|---|---|---|
| 4,117,323 | 9/1978 | Greer et al. | 250/311 |
| 4,206,349 | 6/1980 | Kamimura | 250/311 |
| 4,929,041 | 5/1990 | Vahala et al. | 250/311 |
| 5,171,992 | 12/1992 | Clabes et al. | 250/423 F |
| 5,539,203 | 7/1996 | Ohdomari | 250/492.21 |
| 5,574,280 | 11/1996 | Fujii | 250/492.21 |
| 5,656,811 | 8/1997 | Itoh et al. | 250/492.21 |
| 5,770,861 | 6/1998 | Hirose et al. | 250/492.21 |
| 5,798,529 | 8/1998 | Wagner | 250/492.21 |

*Primary Examiner*—Bruce C. Anderson
*Attorney, Agent, or Firm*—Notaro & Michalos P.C.

[57] ABSTRACT

The invention relates to a ion beam preparation device for electron microscopy which is capable of observing the preparation process with the aid of a scanning electron microscope (3) and hence deliberately operate on the sample (4). The device is fitted with a multi-axis sample bench, at least on ion source (1, 2), a scanning electron microscope (3) with electron detectors (7, 9, 8) to image secondary electrons (SE), back-scatter electrons (RE) and transmitted electrons (TE), an electron source as a discharger for isolating samples and a light microscope (5). The ability to observe the etching process in situ permits precise monitoring of the etching stage, e.g. the degree of thickness reduction of the sample, at high resolution and, with the aid of a control device (19), it is possible automatically to terminate the thinning process to precise instructions.

11 Claims, 2 Drawing Sheets

ION BEAM PREPARATION DEVICE FOR ELECTRON MICROSCOPY

FIELD AND BACKGROUND OF THE INVENTION

The subject of this invention is an ion beam preparation device for processing electron microscopy specimens with a vacuum chamber and at least one ion source for specimen bombardment in a specimen holder by a noble gas ion beam, in particular with argon ions.

For electronmicroscopical observation of specimens the latter must be suitably prepared, e.g. by ion beam etching (D. G. Howit,, Ion Milling of Materials Science Specimens for Electron Microscopy: A Review, Journal of Electron Microscopy Technique 1: 405–414 (1984); A. Garulli, A. Armigliato, M. Vanzi, Preparation of Silicon Specimens for Transmission Electron Microscopy, J. Microsc. Spectrosc. Electron. Vol. 10, No. 2, 1985, 135–144).

Ion etching for preparing specimens used in scanning electron microscopy (SEM) and transmission electron microscopy (TEM) is a method that is principally used where conventional chemical and electrochemical processes fail or yield only inadequate preparation results. This applies in particular to TEM cross-sectional preparation of material and layer combinations with strongly selective etching behavior, and to chemically resistant materials. For these cases ion etching has developed into a routinely practiced method.

Whereas in the beginning cross-section specimens were usually examined with transmission electron microscopes with an acceleration voltage of 100 kV, preference is now given to medium voltage equipment with 300 kV and field emission sources. This equipment ensures uniform transmissibility of the cross-section specimens and is able to form beam probes in the nm range. This establishes the technical preconditions for structural examination and material analysis (EELS, EDX) in the finest details, that is, also on nanostructures.

The development of the nanotechnology, that is, the creation and utilization of structures and dimensions in the submicrometer and nanometer range (e.g. semiconductor component structures), imposes significantly more demanding requirements on the preparation technique. The necessary etching to the desired thickness of structures with extremely small dimensions requires a significantly better observation possibility of the specimen during the etching process so that the momentary stadium of the specimen preparation can be accurately determined.

The currently known, conventional ion beam etching systems such as the RES 010 from BAL-TEC, the PIPS model 691 and the Dual Ion Mill from Gatan, as well as the Ion Beam Thinning Unit from Technology LINDA, use light microscopy with a maximum magnification factor of 100 for observing the specimens. This is generally inadequate already in the cross-section preparation of simple multilayer systems because the moment at which the etching process is terminated cannot be accurately determined. In the case of specimen etching to the desired thickness of selected structures, in-situ evaluation of whether or not the structure of interest is located within the thinned down specimen area is entirely impossible. This applies already to structures (also samples with periodic structures) in the $\mu$m range! As a consequence an elaborate "trial and error" process is needed in which the specimen must be repeatedly transferred between the etching system and the transmission electron microscope or the corresponding specimen holders. This often results in destruction of the specimen.

Another disadvantage of the known ion beam etching systems is the poor controllability of the final stage in the etching process. Neither the optical observability nor the automatic cut-outs known from the known ion beam etching systems allow determination of the exact etching process termination. The sensitivity of the optical and electronic cut-offs used in these equipments is inadequate for switching off the etching process on time. This applies in particular to the ion beam preparation of cross-section specimens. A certain improvement is achieved by the RES 010 from BAL-TEC which uses a special specimen holder with built-in Faraday cup for detecting all charged particles. However, this arrangement severely restricts the possibilities of the specimen holder because the specimen cannot be thinned and observed on the back.

In the known ion beam preparation devices the specimens are usually rotated during the etching process in order to improve the uniformity of erosion. From patent application U.S. Pat, No. 4,128,765 it is known that the specimens should not only be rotated but also the incidence angle of the ion beam should be varied during the etching process based on a random function. This is achieved by a rigid arrangement of the ion sources and by reciprocating the specimen holder containing the probe relative to the ion beam by a certain angle. After the etching process the specimen is ready for electronmicroscopical observation.

In addition to the conventional etching technique described above there is another technique that was initially developed for fault analysis on microelectronic circuits. With the aid of a finely focussed (diam. in nm range) scanning ion beam the specimen can be etched to the desired thickness and observed also through ion microscopy. This focussed ion beam technique (FIB) is currently used also for the preparation of specimens for scanning electron microscopy (SEM) and transmission electron microscopy. For this purpose the specimen areas of interest are partially cut through etching by means of Ga liquid metal ion sources with extremely high ion densities of up to 10 A/cm$^2$, either on one side (slope for SEM examination) or on both sides (ribs for TEM examination). In-situ observation of the etching process is performed with the secondary particles detached by the ion beam (e.g. Hitachi FB 2000, FEI FIB 200, 600 and 800) and lately also with an additional scanning electron microscope (FEI Dual Beam FIB/SEM workstation). The finely focused ion beam and the ability of accurately positioning the specimen and the ion beam allow accurate etching of the specimen to the desired thickness. However, as ion beam etching is only possible with a stationary specimen this results in strongly preferred structures on the etching slope. This is particularly disadvantageous in multilayer systems with strongly selective etching characteristics. The necessarily high ion current density results in strong back-coating of the etching slope and strong heating of the specimen. TEM specimens can only be produced as ribs with a thickness of approx. 100 nm which renders high-resolution TEM (HRTEM)examination in selected specimen areas impossible. As the ribs must be held in place by the remaining specimen material, tilting of the specimen in the TEM for exact specimen orientation is possible only within narrow limits due to the shading effect. For producing TEM specimens the specimen surface must be coated. This FIB (focused ion beam) technique has become known, for example, from the Japanese patent application JP 6231720 which corresponds to U.S. Pat. No. 5,525,806. A strongly focused ion beam is scanned at an angle of 90° across the substrate to be processed, where cuboid areas are worked out of the substrate, leaving thin ribs that form the area of interest for subsequent TEM examination. The arrangement with the scanning ion beam is operated simultaneously as a SIM, that is, as an ion microscope, for observing the etching process. After sufficient etching has occurred on both sides of the rib-shaped area of interest, the area of interest is exposed and the ion source can be switched off. The specimen can subsequently be examined with the SEM.

Simultaneous observation of the specimen during the etching process is possible only with the Dual Beam FEI in SEM mode. In the case of all other equipment the specimen must be moved into an observation position and can be observed only with the ion microscope. Even if a lower ion current density and acceleration voltage are used, the disadvantage is that during the observation material is removed from the specimen area of interest or that bombardment ions are implanted, both of which alter the original specimen material.

SUMMARY OF THE INVENTION

The various features of novelty which characterize the invention are pointed out with particularity in the claims annexed to and forming a part of this disclosure and are entirely based on the German priority application No. 295 07 225.3 filed Apr. 29, 1995.

The purpose of the invention is to eliminate the disadvantages in the current state of the art, and in particular to etch the specimens under accurate control in an economical manner with few rejects.

According to the invention this task is solved by the device of other intention.

The device according to the invention for preparing transmission and scanning electron microscopy specimens allows scanning electron microscopic observation of the specimen during the etching process in the SEM and transmission scanning electron microscopy (TSEM) mode and consequently continuous evaluation of the momentary etching state as well as accurate optical determination of the etching process termination and automatic cut-out of the specimen thinning by means of the transmitted electrons registered by an electron detector (TE detector), without restricting the preparation capabilities of the device.

The device according to the invention comprises of a vacuum chamber with a pump system, at least one ion source for noble gas ion bombardment of the sample in a specimen holder, preferably argon ions, where also more than one, preferably two ion sources can be used for achieving higher etching speeds and consequently shorter preparation times. The specimen holder allows rotation and tilting of the specimen. Through the specimen rotation a homogeneous erosion of the specimen surface is achieved during the ion etching process and the ability to tilt the specimen improves the variation width of the preparation parameters, e.g. the angle of incidence.

On the vacuum chamber the column of a scanning electron microscope is mounted, the longitudinal axis of which is directed toward the specimen. At least a first electron detector comprising, for example, a scintillator, fibre optic and photomultiplier for registering the secondary electrons (SE detector) is arranged with a certain tilt relative to the longitudinal axis of the SEM column so that the specimen holder and the detector, even at different tilting angles of the specimen holder, are always in a position that is favorable for obtaining an adequate electron signal in the SE detector. In contrast to the present state of the art the specimen can thus be observed with a resolution in the nm range, allowing accurate evaluation of the preparation process stage which is of fundamental importance to the systematic preparation of microfine structures (etching to desired thickness).

A second electron detector, preferably a semiconductor detector for registering the transmitted electrons (TE detector), is arranged in the axial direction of the SEM column behind the specimen and allows transmission scanning electron microscopic (TSEM) imaging of the electron transparent areas of the specimen to be thinned down. In this way an in-situ decision with a resolution in the nm range can be made on how well the specimen is transparent for electrons, whether or not in the case of specimen etching to the desired thickness the structures of interest are located within the electron transparent area of the specimen, and whether the etching process should be continued or terminated. The structures can be gauged in-situ and consequently differentiated through line width measurement under software control of the scanning electron microscope. The possibility of in-situ evaluation of the preparation result and the etching process termination point immediately in the ion beam etching device is another significant advantage over the present state of the art.

For this purpose the TE detector is equipped with a control device that is coupled to the power supply of the ion source and which can switch off the ion source when a preset detector current is registered. This automatic cut-out is much more sensitive than the known automatic cut-outs, and interrupts the etching process before, for example, a hole occurs in the specimen.

The microscope and the electron detectors are preferably protected against contamination by lockable shutters during the etching of the specimen. Protection of the sensitive electron detector components and the scanning electron microscope significantly enhances the reproducibility of the specimen observation and the service life between cleaning.

Because of its mobility in the x, y and z axes the specimen holder can be centered relative to the axial direction of the microscope, and the working distance between the microscope and the specimen holder can be adjusted which means that the specimen can be moved from the preparation position to the optimum working distance of the microscope and subsequently restored to the preset working position.

The ion sources used in this arrangement supply a rigid, focused noble-gas ion beam with ion current densities below 100 mA/cm$^2$, preferably below 30 MA/cm$^2$, in order to achieve a short etching time combined with gentle specimen preparation.

Directly below the exit opening of the scanning electron microscope it is possible to install, for example, a third electron detector, preferably a semiconductor detector, for registering the back scattered electrons (BSE detector) so that the specimen can be imaged additional and selectively either in mass contrast or topography contrast.

At least one ion source, preferably two ion sources, can be tiltably arranged relative to the specimen holder which allows a large variation width of the preparation conditions such as the specimen bombardment angle as well as one-sided and concurrent two-sided specimen etching.

The invention offers the advantage that the SEM column, electron detectors, ion sources and specimen holders are arranged in such a way that the ion beam preparation of the specimen can be observed in-situ at any time, independently of the preparation conditions in the device and without interrupting the preparation process.

A light microscope connected to the vacuum chamber is used for observing the adjustment of the ion beam relative to the specimen. Due to the required accuracy this adjustment can only be performed with a light microscope.

In the SEM observation of isolating specimens during the ion beam processing the bombarding ions compensate the negative specimen charge caused by the electron beam of the SEM. In the ion beam processing of isolating specimens it is advantageous to compensate the positive charge caused by the electron beam of the SEM because in this way uninfluenced specimen preparation and simultaneously interference-free imaging of the specimen is possible.

When an isolating specimen is examined at the optimum working distance of the SEM with the ion source switched off, the negative specimen charge can be compensated by means of an electron source that is aimed at the specimen and operates with electrons in the energy range of 300 eV to 1500 eV, preferably 400 eV to 1000 eV. Electrons within this energy range have a secondary electron yield >1 and therefore create an electron impoverishment in the specimen which leads to the compensation of its negative charge.

BRIEF DESCRIPTION OF THE DRAWINGS

The invention is subsequently explained in more detailed based on a design example and references to the drawings. These drawings show:

FIG. 2a during the preparation of the first specimen side the specimen can be observed by means of the SE detector and RE detector.

FIG. 2b for high-resolution observation the specimen is located within the optimum working distance of the SEM.

FIG. 2c during the preparation of the second specimen side up to the electron transparency of the specimen, the specimen can be observed with the SE detector and BSE detector as well as the TE detector. If the final thinning control is performed with the TE detector, a shutter is positioned in front of the SEM column and the SE detector which protects these components against contamination by ion beam etching.

DESCRIPTION OF THE PREFERRED EMBODIMENTS

Figure 1:
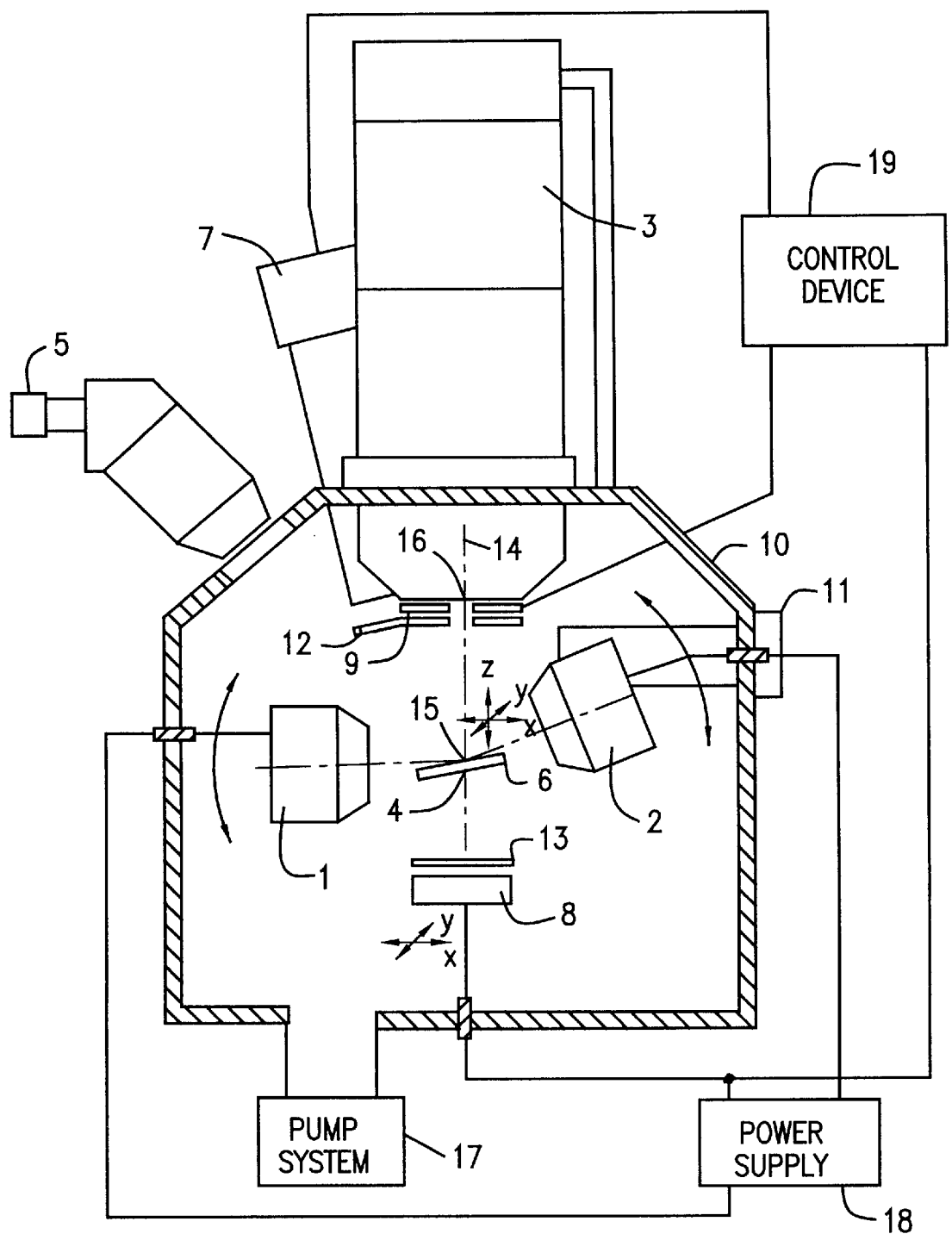
FIG. 1 is a Schematic illustration of the device for ion beam preparation of specimens used in electron microscopy, with a SEM observation possibility.

A design example of the device according to the invention for ion beam preparation of specimens used in electron microscopy with scanning electron microscopic observation possibility is schematically illustrated in FIG. 1. The column of the SEM 3 is mounted perpendicularly on vacuum chamber 10 which can be pumped down to an ultimate pressure of 10–6 Torr by a pump system 17. SEM column 3 protrudes 90 mm into the vacuum chamber and its longitudinal axis 14 is aligned to specimen 4 located in specimen holder 6.

Specimen holder 6 is mounted at a distance of 50 mm from the underside of SEM column 3, preferably on a 5-axis specimen stage that allows mobility as follows:

Rotation and oscillating movement of specimen 4

Tilting around the longitudinal axis of the specimen holder by 0 to 360°

X movement ±15 mm

Y movement ±15 mm z movement ±40 mm (movement direction specimen holder 6/SEM column 3)

Two opposite ion sources 1 and 2, for example saddle field ion sources that work with an acceleration voltage of 1–10 kV at an ion current density of up to 20 mA/cm$^2$ and a beam diameter of approx. 0.5 mm, the beam of which is aimed at specimen 4, are mobile relative to specimen holder 6 where specimen holder 6 and the ion sources 1, 2 are mutually swivel mounted around a central axis of rotation 15. The utilization of two ion sources is advantageous because this shortens the preparation time and enhances the variation possibilities for the preparation conditions. Ion sources 1, 2 can be swiveled jointly or individually around the central axis 15, and individually around an additional axis of rotation.

Tilted by an angle of 45° relative to the longitudinal axis of SEM column 3 the light microscope 5 is arranged which is principally used for observing the ion beam alignment relative to specimen 4.

A secondary electron detector 7, preferably of the Everhart Thornley type, is arranged with an offset of 45° relative to light microscope 5 and at an angle of 60° relative to the longitudinal axis 14 of the SEM. In this way a favorable secondary electron detection position of SE detector 7 relative to specimen 4 and consequently the imaging of the specimen surface is continually possible, independently of the specimen holder 6 tilting angles used in the device.

Figure 2A:
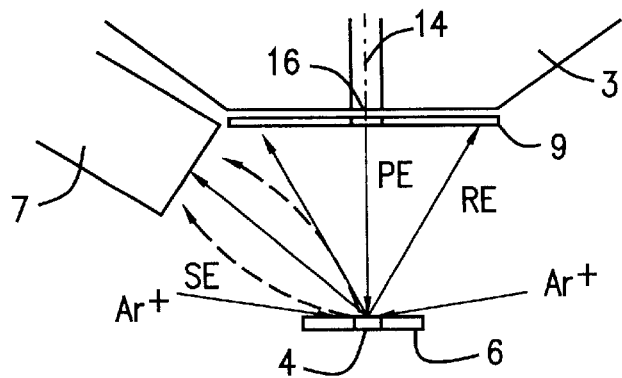
FIGS. 2a, 2b and 2c are schematic illustrations of the SEM column, specimen holder in horizontal position, SE detectors, RE detector, TE detector and shutters.

As shown in FIG. 2a specimen 4 can be observed in-situ with high resolution of a scanning electron microscope at any time during the etching process, independently of the selectable preparation conditions of the device and without interrupting the etching process. The advantage is that the status of the specimen preparation in the z direction and the accuracy of specimen etching to the desired thickness in the x, y, plane can be assessed at any time.

In the layout described above the bombardment angles can be varied as follows:

When specimen holder 6 is tilted by 15° relative to the light microscope 5 the bombardment angle of the first ion source 1 can be varied from −20° to 40°, and the bombardment angle of the second ion source 2 from −40° to 15°, where 0° corresponds to parallel ion incidence relative to the specimen surface.

If only the first ion source 1 is used, the ion incidence angle relative to specimen 4 can be varied between 0° and 70° by tilting specimen holder 6 by 45° out of the horizontal position. Specimen 4 always remains in a favorable observation position to the SEM.

Figure 2B:
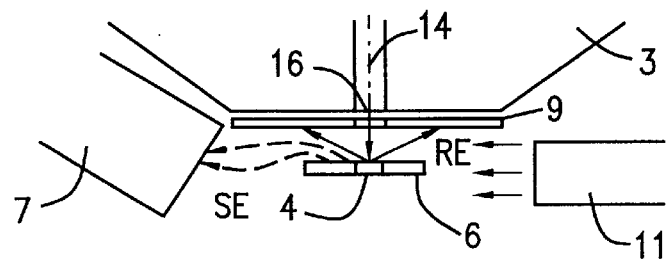

For specimen surface observation with higher resolution specimen 4 can be moved via a 40 mm distance path from the preparation position to the optimum working distance of the scanning electron microscope of 8 to 12 mm as shown in FIG. 2b. After the examination it can be restored exactly to the preset initial position without having to change the arrangement of the ion sources or the tilting angle of the specimen holder.

Directly adjacent to SEM column 3 there is an electron source 11 aimed at specimen 4 that supplies electrons with energies of 400 eV to 1000 eV and is used for discharging isolating specimens during the SEM observation at the optimum working distance.

Figure 2C:
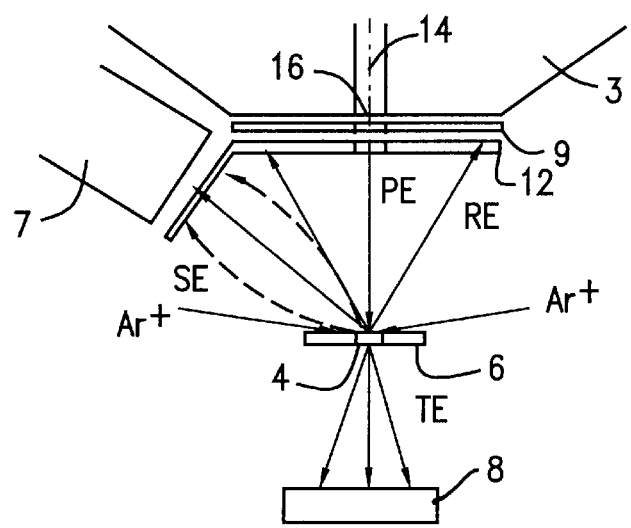

Below the specimen there is a second electron detector 8 that can be shifted in the x, y direction, preferably a semiconductor detector for registering the transmitted electrons where said detector is used in the final thinning process of the second specimen side as shown in FIG. 2 and is coupled to power supply 18 of the ion source via a control device 19, for example, a computer control. When specimen 4 become electron transparent this can be observed on the monitor of the scanning electron microscope either through light or dark field imaging in TSEM mode, and the ion sources are switched off with the aid of the registered detector current in accordance with a set point. In contrast to the known solutions this automatic cut-out is highly sensitive and eliminates unwanted puncturing of the probe.

Subsequently the high-resolution TSEM mode is used to evaluate whether the structures of interest are located within the electron transparent area of specimen 4 and whether or not specimen 4 needs to be further thinned or the etching process should be terminated. The structures can be gauged in-situ and thus differentiated by means of line width measurement via the software of the scanning electron microscope.

An BSE detector 9 in the form of the semiconductor quadrant detector is arranged directly below the exit opening 16 of the scanning electron microscope so that the specimen surface can optionally be imaged in mass contrast or topography contrast.

The device consequently allows optimum control of the etching process at all times which is particularly significant in systematic thinning of selected structures (specimen etching to the desired thickness) so that the ion etching process can be terminated at the correct moment.

Another advantage of the device according to the invention is that based on the high variation width of the bombardment angle and the different positioning possibilities of the specimen holder 6, specimens can be produced with high precision not only for transmission electron microscopy (laterally thinned specimens and cross-section specimens) but also for scanning electron microscopy (e.g. etch slope-cuttings).

During the etching process SEM column 3 and electron detectors 7, 8, 9 can be protected against contamination from sputtered sample material by means of shutters 12, 13 that can be swung into the path, where shutter 12 for the SEM column functions as an electron beam opening so that the final stage of the thinning process can still be continuously controlled by means of TE detector 8. In the following two examples of specimens prepared with said arrangement shall be introduced:

Example 1 relates to lateral preparations of a semiconductor component structure. The specimen has been mechanically thinned from the substrate side to the ion etching starting thickness of 35 μm. The ion etching was subsequently performed on the substrate side with two ion sources under a bombardment angle of 6° relative to the specimen surface and an acceleration voltage of 9.8 kV under SEM control until electron transparentness of the specimen was achieved.

The second example relates to the cross-sectional preparation of a contact hole structure of a multilayer circuit system. The initial thickness of the specimen, achieved by mechanical preparation, was 35 μm. The specimen was subsequently thinned down to a predefined depth from the first side by means of an ion source under a bombardment angle of 4° and an acceleration voltage of 8 kV with oscillating specimen movement under SEM control. The ion beam preparation of the second specimen side up to the electron transparency of the specimen was performed in the same way. The final stage of the thinning process of both specimens was successfully controlled with the aid of the TE detector. As soon as the specimens were electron transparent a picture with the structures of interest appeared on the monitor of the SEM and the etching process was terminated on time.

SUMMARY

The invention relates to an ion beam preparation device for electron microscopy that can observe the preparation process with the aid of a scanning electron microscope (3) and is consequently able to systematically process the specimen (4). The device is equipped with a multi-axis specimen stage, at least one ion source (1, 2), a scanning electron microscope (3) with electron detectors (7, 9, 8) for monitoring secondary electrons (SE), back scatter electrons (BSE) and transmitted electrons (TE), an electron source (11) as a discharge device for isolating specimens, as well as a light microscope (5).

The ability to observe the etching process in-situ allows accurate control of the etching state, e.g. the degree of specimen thinning, with high resolution, and with the aid of a control device (19) the thinning process can be automatically terminated based on a setpoint.

I claim:

1. Ion beam preparation device for processing specimens (4) used in electron microscopy, comprising a vacuum chamber (10) and at least one ion source (1, 2) for bombarding a specimen (4) in a specimen holder (6) with noble gas ions for etching the specimen, means for allowing stationary ion beam impingement on the specimen (4) at a predefined angle, means for rotating and for tilting the specimen holder (6) into a fixed position, the vacuum chamber (10) having an SEM column (3) with an axis (14) aimed at the specimen (4), a first scanning electron microscope (SEM) detector (7) with means for imaging the specimen surface during operation of the ion source for bombarding the specimen, and a second SEM detector (8) with means for imaging the specimen in TSEM mode by registering electrons transmitted through the specimen during operation of the ion source for bombarding the specimen, the first and second detectors imaging the specimen continuously during the etching with noble gas ions.

2. Device according to claim 1 where the second detector (8) is arranged behind specimen (4) along the axis (14) of the electron microscope (3).

3. Device according to claim 2 where the second detector (8) is connected to a control device (19) which is coupled to the ion source (1, 2) in such a way that the ion source (1, 2) is switched off when a preset detector current is attained based on visibly predefined structure elements in the SEM image in accordance with a degree of specimen etching.

4. Device according to claim 1 where a lockable shutter (12) is arranged in front of a microscope opening (16) of microscope (3) and at least in front of the first detector (7).

5. Device according to claim 1 where specimen holder (6) centers the specimen (4) on the axis (14) of a microscope and the working distance between specimen (4) and microscope (3) is adjustable.

6. Device according to claim 1 where the specimen holder (6) is mobile in five axes.

7. Device according to claim 1 where the ion current density on specimen (4) is not greater than 100 mA/cm$^2$.

8. Device according to claim 1 where a third scanning electron microscope (SEM) detector (9) is provided as a back scatter electron detector arranged directly around the scanning electron microscope exit opening (16).

9. Device according to claim 1 including means so that at least one ion source (1, 2) can be swiveled relative to specimen (4).

10. Device according to claim 1 where on vacuum chamber (10) a light microscope (5) is arranged which allows observation of the ion beam alignment relative to the specimen (4).

11. Device according to claim 1 where the device comprises an electron source (11) that is aimed at specimen (4) where said electron source (11) comprises means for creating electron energies, for example, of 300 electron Volt to 1500 electron Volt and preferably 400 electron Volt to 1000 electron Volt.

* * * * *